United States Patent [19]

Weigert

[11] Patent Number: 4,754,084
[45] Date of Patent: Jun. 28, 1988

[54] PREPARATION OF SUBSTITUTED FLUOROBENZENES

[75] Inventor: Frank J. Weigert, Wilmington, Del.

[73] Assignee: E. I. Du Pont de Nemours and Company, Wilmington, Del.

[21] Appl. No.: 32,634

[22] Filed: Apr. 1, 1987

[51] Int. Cl.$^4$ .................. C07C 17/24; C07C 17/26; C07C 25/13; C07C 25/22
[52] U.S. Cl. ................. 570/146; 570/127; 570/129; 570/144
[58] Field of Search .................. 570/146, 144

[56] References Cited

U.S. PATENT DOCUMENTS

| | | | |
|---|---|---|---|
| 2,441,128 | 5/1948 | Barrick et al. | 260/464 |
| 2,462,347 | 2/1949 | Barrick | 260/85 |
| 2,861,095 | 11/1958 | Drysdale | 260/464 |
| 3,499,942 | 3/1970 | Nefedov et al. | 260/649 |
| 3,637,871 | 1/1972 | Park et al. | 570/146 |

*Primary Examiner*—J. E. Evans

[57] ABSTRACT

Substituted fluorobenzenes are produced by pyrolyzing vinylfluorocyclobutanes at a temperature of 250°–450° C. in the presence of activated carbon or certain metal oxides or mixtures of metal oxides.

14 Claims, No Drawings

PREPARATION OF SUBSTITUTED FLUOROBENZENES

BACKGROUND OF THE INVENTION

Substituted fluorobenzenes are known in the art and have found utility as intermediates, particularly for making insecticides, fungicides and herbicides. They are also useful for drugs or intermediates for drugs.

U.S. Pat. No. 2,861,095 relates to certain fluorocyclohexenes and to methods for their preparation. The patent describes a method for pyrolyzing vinylfluorocyclobutanes to fluorocyclohexenes at temperatures of 450°–800° C. The patent discloses at column 1, line 67 that temperatures above 800° C. are undesirable because of the tendency of the vinylfluorocyclobutanes to be converted to difluorobenzenes rather than to the desired cyclohexenes.

U.S. Pat. No. 3,499,942 discloses a process for making carbocyclic mono- and difluoroaromatic compounds by pyrolysis of an aliphatic fluorine containing compound with a conjugated compounds, e.g., a cyclic diene, at temperatures at 300°–800° C. Example 25 of the patent describes the pyrolysis of a mixture of butadiene and tetrafluoroethylene in the absence of an additional reagent at 600° C. to produce a mixture of isomeric difluorobenzenes.

SUMMARY OF THE INVENTION

The present invention is related to an improvement in these processes which makes them particularly useful for making substituted fluorobenzenes.

In the process of the invention vinylfluorocyclobutanes having at least two fluorine atoms on the same ring carbon are pyrolyzed at a temperature of 250°–450° C. in the presence of activated carbon or an oxide of Al, Ti, Ce or Cr alone or in combination with another metal oxide, such as the oxides of Al, Ti, Ce, Cr, Fe, Co, Ni, Mo, Mn, Zn, Cu, Ag, V, La, W, Zr, Si, Bi, P, Pb or mixtures thereof.

The major advantage in conducting the pyrolysis of vinylfluorocyclobutanes in the presence of the reagents of this invention is a noted increase in reaction rate and/or a difference in product composition, i.e. it can provide selectivity toward desired products.

DESCRIPTION OF THE INVENTION

The process of the invention makes substituted fluorobenzenes from a vinylfluorocyclobutane with at least two fluorines on the same carbon of the four-membered ring. Exemplary of the cyclobutanes which can be used in the process of the invention are those represented by the following structure:

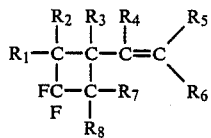

wherein
$R_1$ and $R_2$ are independently H, F, $CF_3$, Cl or Br, provided that unless $R_1$ and $R_2$ are both Cl, one of $R_1$ and $R_2$ is F;
$R_3$ is H, $CH_3$, $C_2H_5$ or Cl;
$R_4$ is H, $CH_3$, $C_2H_5$ or Cl;
$R_5$ and $R_6$ are independently H, Cl, $CH_3$ or $C_2H_5$, provided that one of $R_5$ and $R_6$ must be H, and further provided that when $R_6$ is H, $R_4$ and $R_5$ can be combined to form $-CR_9=CR_9-CR_9=CR_9-$ where at least three of the $R_9$ are H and the other $R_9$ can be H, Cl, Br, F or $CF_3$; and
$R_7$ and $R_8$ are independently H or $CH_3$, provided that one must be H.

The above starting vinylfluorocyclobutanes can be prepared by reacting a 1,1-difluoroethylene with a suitable diene by the process described in U.S. Pat. No. 2,462,347 to P. L. Barrick. Or they can be prepared by the method of P. L. Barrick and Richard D. Cramer disclosed in U.S. Pat. No. 2,441,128.

In the process of the invention the vinylfluorocyclobutanes can be made separately and then fed into the process of the invention.

The starting material is then converted into the desired fluorobenzenes by pyrolyzing them, preferable in an inert atmosphere, at temperatures of 250°–450° C. while in the presence of a reagent.

During the course of the reaction the reagents are converted to fluorides by interaction with liberated hydrogen fluoride. These fluorides do not function as catalysts for the overall reaction. Therefore the reagents are not catalyst in the strict sense of the definition since they are consumed in the process of the reaction.

Reagents which are useful in the process of the invention are certain metal oxides or mixtures thereof and activated carbon. The useful metal oxides are the oxides of aluminum, titanium, cerium or chromium. These oxides can be used alone, or in combination with other metal oxides, such as one or more of the oxides of Fe, Co, Ni, Mo, Mn, Zn, Cu, Ag, V, La, W, Zr, Si, Bi, P, or Pb. The combination of oxides can be obtained by supporting or mounting the additional metal oxide on a support of the aluminum, titanium, cerium or chromium oxide, e.g., $Fe_2O_3$ supported on an activated alumina carrier. In some instances the oxides of alumina, titanium, cerium or chromium can be employed with a precious metal, e.g., a reagent of 0.5% Pd on $Al_2O_3$.

The choice of the other metal oxide can have an effect on the selectivity or reaction rate of the process.

The preferred reagent is $Al_2O_3$.

The reagent must be present in an effective amount. The reagent's purpose is to absorb or react with liberated HX, [X=F, Cl]. The balanced equation of alumina with HF is as follows:

$$Al_2O_3 + 6HF \rightarrow 2AlF_3 + 3H_2O.$$

One skilled in the art can use this equation, or any balanced equation with respect to the oxide used, to calculate the amount of reagent needed based on the amount of HX that would be liberated from the reaction. In practice it is usually desired to use an excess of reagent because the surface of the oxide becomes coated with a fluoride, e.g., $Al_2O_3$ quickly becomes coated with $AlF_3$, and the reaction would then become diffusion controlled. Therefore in the case of the oxide reagents, the effective amount of reagent means 2 to 10 times the number of moles of HX that would be liberated during the course of the reaction.

The mechanism with respect to the use of activated carbon as a reagent is not known. In practice, the effective amount of carbon that is needed is 2 to 50 times the number of moles of HX that would be liberated during the course of the reaction.

When $R_1$, $R_2$, or $R_9$ is $CF_3$ activated carbon should be used as the reagent. By activated carbon is meant an amorphous carbon having high adsorptivity for gases, vapors, and colloidal solids. Such activated carbons are typically formed from the carbon source by heating to about 800° C. to 900° C. with steam or carbon dioxide to confer upon the carbon a porous internal structure.

No air or oxygen should be present in the reaction at any time. This can be accomplished by conducting the reaction only with the organic vinylfluorocyclobutane and reagent present and this is a preferred embodiment.

In an optional embodiment, the process of the invention can be conducted in an inert atmosphere. Inert atmospheres which are suitable for the process of this invention include nitrogen, helium and argon.

The pyrolysis temperature of the process of the invention can range between 250° C. and 450° C. The preferred temperature range is 300° C. to 400° C. The pyrolysis can be conducted in the pressure range of 0.1 to 10 atmospheres. The preferred range is 1 to 2 atmospheres and atmospheric is most preferred.

The process of the invention is operated in the vapor phase and conventional techniques and apparatus can be employed. For example, the vinylfluorocyclobutane starting materials can be introduced into a reactor by vaporizing a designated flow into a stream of inert gas. If necessary, the starting vinylfluorocyclobutane can be dissolved in a suitable solvent, e.g., benzene. The contact time of the reagent and starting material is not critical and can range from 0.1 sec to 1.0 min, with the preferred range being from 2 sec to 10 sec. The reactor can be a tube made of heat-resistant glass, quartz, or metals such as stainless steel, nickel, or Hastelloy, and packed with an inert material. An electric heater can be employed to heat the reaction zone.

The fluorobenzenes produced by the process of this invention can have the following structure:

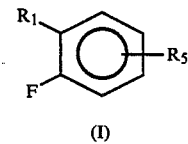 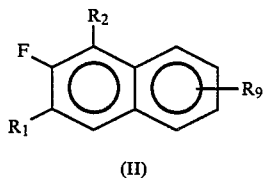

(I)            (II)

wherein $R_1$ and $R_2$ are as previously described, i.e., H, F, $CF_3$, Cl or Br, provided that one of $R_1$ or $R_2$ in Structure II is hydrogen, $R_5$ is H, Cl, $CH_3$ or $C_2H_5$, and $R_9$ is Cl, Br, F, $CH_3$ or $CF_3$.

When $R_1$ or $R_2$ is F or Cl, Structure I may contain two additional $CH_3$ groups.

The process of the invention provides selectivity for the production of fluorobenzene, 2-chloro and 2-bromofluorobenzene, which are fungicide intermediates, and 1 2-difluorobenzene, which is a herbicide intermediate.

The following examples are offered to illustrate the process of the invention.

The following general procedure was employed for all the examples. A liquid flow of 1 ml/hr vinylfluorocyclobutane and a gas flow of 5 ml/min of inert gas was directed through a ¾"×5" Vycor reactor filled with the indicated reagent or inert material at the designated temperature. The reactor was heated externally by an electrical heater. Various inert materials such as silicon carbon were employed in the comparative experiments. The effluent from the reactor was cooled, condensed and analyzed by GC and/or fluorine NMR.

EXAMPLE 1

The general procedure was followed using a mixture of 1-(2-propenyl)-2,2,3,3-tetrafluorocyclobutane and 1-methyl-1-vinyl-2,2,3,3-tetrafluorocyclobutane in a ratio of 25:75 as the liquid feed and nitrogen gas as the inert carrier. The reactor was charged with 3 g of AL-0104 (tableted activated alumina containing 99% $Al_2O_3$). At 350° C. the conversion was 15% and the yield of difluorotoluenes was 67% consisting of 41% 2,3-difluorotoluene and 59% 3,4-difluorotoluene.

The above experiment was repeated using 19 g of SiC in place of the 3 g of AL-0104. At 450° C. the conversion was 28%. The yield of difluorotoluenes was 26% consisting of 89% of 2,3-difluorotoluene and 11% 3,4-difluorotoluene.

EXAMPLE 2

The general procedure was followed using 1-methyl-1-(2-propenyl)-2,2,3,3-tetrafluorocyclobutane as the liquid feed at a flow rate of 1 ml/hr and nitrogen gas as the inert carrier. The reactor was charged with 5 g of AL-0104 (tableted activated alumina containing 99% $Al_2O_3$). At 400° C. the conversion was 100% and the composition of the dimethyldifluorobenzenes was 40% 1,4-dimethyl-2,3-difluorobenzene, 54% 1,2-dimethyl-4,5-difluorobenzene and 6% 1,3-dimethyl-4,5-difluorobenzene.

The above experiment was repeated using 19 g of SiC in place of the 5 g of AL-0104. At 500° C. the conversion was 71% and produced 19% of 1,4-dimethyl-2,3-difluorobenzene.

EXAMPLE 3

The general procedure was followed using a mixture of 1-methyl-1-(1-propenyl)-2,2,3,3-tetrafluorocyclobutane and 1-methyl-2-(2-propenyl)-3,3,4,4-tetrafluorocyclobutane as the liquid feed at a flow rate of 0.5 ml/hr. Nitrogen gas was used as the inert carrier. The reactor was charged with 3 g of AL-0104 (tableted activated alumina containing 99% $Al_2O_3$). At 400° C. the yield of 1,3-dimethyl-4,5-difluorobenzene was 43%.

The above experiment was repeated using 18.5 g of SiC in place of the 3 g of AL-0104. At 450° C. the yield of 1,3-dimethyl-4,5-difluorobenzene was 18%.

EXAMPLE 4

The general procedure was followed using 1-methyl-2-(1-propenyl)-3,3,4,4-tetrafluorocyclobutane as the liquid feed at a flow rate of 1 ml/hr. Nitrogen gas was used as the inert carrier. The reactor was charged with 5 g of AL-0104 (tableted activated alumina containing 99% $Al_2O_3$). At 450° C. the yield of 1,4-dimethyl-2,3-difluorobenzene was 42%.

The above experiment was repeated using 19 g of SiC in place of the 5 g of AL-0104. At 500° C. only a trace of 1,4-dimethyl-2,3-difluorobenzene was produced.

EXAMPLE 5

The general procedure was followed using a mixture of 1-chloro-1-vinyl-3,3,4,4-tetrafluorocyclobutane and 1-(1-chloroethenyl)-2,2,3,3-tetrafluorocyclobutane as the liquid feed at a flow rate of 1 ml/hr. Nitrogen gas was used as the inert carrier. The reactor was charged with 3 g of AL-0104 (tableted activated alumina containing 99% Al₂O₃). At 400° C. the combined yield of 1-chloro-2,3-difluorobenzene and 1-chloro-3,4-difluorobenzene was 6%. The above experiment was repeated using 19 g of SiC in place of the 3 g of AL-0104. No 1-chloro-2,3-difluorobenzene or 1-chloro-3,4-difluorobenzene were formed at 400° C.

EXAMPLE 6

The general procedure was followed using 1-(3-propenyl)-2,2,3,3-tetrafluorocyclobutane as the liquid feed at a flow rate of 1 ml/hr. Nitrogen was used as the inert carrier. The reactor was charged with 5 g of AL-0104 (tableted activated alumina containing 99% Al₂O₃). At 300° C. the yield of 1-ethyl-3,4-difluorobenzene was 9%.

The above experiment was repeated using 19 g of SiC in place of the 5 g of AL-0104. No 1-ethyl-3,4-difluorobenzene was produced at 500° C.

EXAMPLE 7

The general procedure was followed using 1-(1-propenyl)-2-chloro-2,3,3-trifluorocyclobutane as the liquid feed at a flow rate of 1 ml/hr. Nitrogen gas was used as the inert carrier. The reactor was charged with 5 g of AL-0104 (tableted activated alumina containing 99% Al₂O₃). At 400° C. the yield of the produced aromatic products was 55% 1-methyl-3-chloro-4-fluorobenzene and 14% 1-methyl-3,4-difluorobenzene.

The above experiment was repeated using 19 g of SiC in place of the 5 g of AL-0104. At 500° C. the only aromatic product produced was 1-methyl-3,4-difluorobenzene.

EXAMPLE 8

The general procedure was followed using a mixture of 1-(2-propenyl)-2-chloro-2,3,3-trifluorocyclobutane and 1-methyl-1-vinyl-2-chloro-2,3,3-trifluorocyclobutane as the liquid feed at a flow rate of 1 ml/hr. Nitrogen gas was used as the inert carrier. The reactor was charged with 3 g of AL-0104 (tableted activated alumina containing 99% Al₂O₃). At 400° C. the yield of the produced aromatic products was 12% combined yield of 1-methyl-2,3-difluorobenzene and 1-methyl-3,4-difluorobenzene and a combined yield of 88% of 1-methyl-2-chloro-3-fluorobenzene and 1-methyl-3-chloro-4-fluorobenzene.

The above experiment was repeated using 19 g of SiC in place of the 3 g of AL-0104. At 500° C. no 1-methyl-2,3-difluorobenzene, 1-methyl-3,4-difluorobenzene, 1-methyl-2-chloro-3-fluorobenzene or 1-methyl-3-chloro-4-fluorobenzene were produced.

EXAMPLE 9

The general procedure was followed using 1-vinyl-2,2-dichloro-3,3-difluorocyclobutane as the liquid feed at a flow rate of 1 ml/hr. Nitrogen was used as the inert carrier. The reactor was charged with 3 g of Al₂O₃. At 350° G the yield of o-chlorofluorobenzene was 65%.

The above experiment was repeated using 19 g of SiC in place of the 3 g of Al₂O₃. At 450° C. the yield of o-chlorofluorobenzene was 3.5%.

EXAMPLE 10

The general procedure was followed using 1-(propenyl)-2,3,3-trifluorocyclobutane as the liquid feed at a flow rate of 1 ml/hr. Nitrogen was used as the inert carrier. The reactor was charged with 5 g of AL-0104 (tableted activated alumina containing 99% Al₂O₃). At 250° C. the conversion was 100% and the yield of 1-methyl-3-fluorobenzene was 89% of the total products produced.

The above experiment was repeated using 19 g of SiC in place of the 5 g of AL-0104. No 1-methyl-3-fluorobenzene was produced at 250° C.

EXAMPLE 11

The general procedure was followed using 1-methyl-1-(2-propenyl)-2-chloro-2,3,3-trifluorocyclobutane as the liquid feed at a flow rate of 1 ml/hr. Nitrogen was used as the inert carrier. The reactor was charged with 5 g of AL-0104 (tableted activated alumina containing 99% Al₂O₃). At 400° C. the composition of the produced aromatics was 58% 1,2-dimethyl-4-chloro-5-fluorobenzene and 42% 1,2-dimethyl-4,5-difluorobenzene.

The above experiment was repeated using 18 g of SiC in place of the 5 g of AL-0104. At 600° C. the composition of the produced aromatics was 15% 1,2-dimethyl-4-chloro-5-fluorobenzene and 85% 1,2-dimethyl-4,5-difluorobenzene.

EXAMPLE 12

The general procedure was followed using 1.85 g of 1-vinyl-2-bromo-2,3,3-trifluorocyclobutane dissolved in 9.75 g of benzene as the liquid feed at a flow rate of 1 ml/hr. Nitrogen was used as the inert carrier. The reactor was charged with 3 g of AL-0104 (tableted activated alumina containing 99% Al₂O₃). At 450° C. the composition of the produced aromatic product was 47% o-bromofluorobenzene, 28% m-bromofluorobenzene and 25% o-difluorobenzene.

The above experiment was repeated using 18 g of SiC in place of the 3 g of AL-0104. At 450° C. some o-difluorobenzene was formed. No brominated aromatic products were produced.

EXAMPLE 13

The general procedure was followed using 11.0 g of 1-vinyl-2-trifluoromethyl-2,3,3-trifluorocyclobutane dissolved in 11.15 g of benzene as the liquid feed at a flow rate of 1 ml/hr. Nitrogen was used as the inert carrier. The reactor was charged with 2.0 g of activated carbon. At 400° C. 41% of o-trifluoromethylfluorobenzene was produced.

The above experiment was repeated using 17.8 g of SiC in place of the activated carbon. At 400° C. no o-trifluoromethylfluorobenzene was produced.

The above experiment was repeated using 4 g of AL-0104 (tableted activated alumina containing 99% Al₂O₃) in place of the carbon. At 400° C. no o-trifluoromethylfluorobenzene was produced.

EXAMPLE 14

The general procedure was followed using 1-(1-propenyl)-2-trifluoromethyl-2,3,3-trifluorocyclobutane as the liquid feed at a flow rate of 1 ml/hr. Nitrogen was used as the inert carrier. The reactor was charged with 3 g of activated carbon. At 550° C. 17% of 2-trifluoromethyl-3-fluorotoluene was produced.

The above experiment was repeated using 19.6 g of SiC in place of the carbon. At 550° C. 3% of 2-trifluoromethyl-3-fluorotoluene was produced.

EXAMPLE 15

The general procedure was followed using 2-(2-propenyl)-2-methyl-3-trifluoro-2,3,3-trifluorocyclobutane as the liquid feed at a flow rate of 1 ml/hr. Nitrogen was used as the inert carrier. The reactor was charged with 3 g of activated carbon. At 400° C. 9% of 1,2-dimethyl-4-trifluoromethyl-5-fluorobenzene was produced.

The above experiment was repeated using 18 g of SiC in place of the carbon. At 500° C. no 1,2-dimethyl-4-trifluoromethyl-5-fluorobenzene was produced.

The above experiment was repeated using 3 g of AL-0104 (tableted activated alumina containing 99% $Al_2O_3$) in place of the carbon. At 350° C. no 1,2-dimethyl-4-trifluoromethyl-5-fluorobenzene was produced.

EXAMPLE 16

The general procedure was followed using 1-(1-chloro-1-ethenyl)-2-trifluoromethyl-2,3,3-trifluorocyclobutane as the liquid feed at a flow rate of 1 ml/hr. Nitrogen was used as the inert carrier. The reactor was charged with 3 g of activated carbon. At 400° C. 2-trifluoromethyl-4-chlorofluorobenzene and 2-trifluoromethyl-5-chlorofluorobenzene were produced.

The above experiment was repeated using 18 g of SiC in place of the carbon. At 400° C. no 2-trifluoromethyl-4-chlorofluorobenzene or 2-trifluoromethyl-5-chlorofluorobenzene was produced.

EXAMPLE 17

The general procedure was followed using a mixture of 1-(2-propenyl)-2,2,3,3-tetrafluorocyclobutane and 1-methyl-1-vinyl-2,2,3-3-tetrafluorocyclobutane as the liquid feed and nitrogen as the inert carrier gas. The reactor contained 3 g of the designated reagent, usually in the form of ⅛ in. tablets. The results of these experiments are given in the following table.

TABLE I

| Run | Reagent | Temp. | Conversion | Yield | Selectivity |
|---|---|---|---|---|---|
| 1 | 20% $Fe_2O_3$ on activated alumina | 400° C. | 24% | 7% | 86 |
| 2 | 10% Cobalt oxide on activated alumina | 400° C. | 79% | 23% | 78 |
| 3 | 19% Manganese dioxide on activated alumina | 400° C. | 41% | 14% | 80 |
| 4 | 10% ZnO & 10% $Cr_2O_3$ on activated alumina | 300° C. | 10% | 2% | — |
| 5 | 10% Zno & 10% $Cr_2O_3$ on activated alumina | 400° C. | 58% | 7% | 86 |
| 6 | 24% Zinc oxide on activated alumina | 300° C. | 4% | 1% | — |
| 7 | 24% Zinc oxide on activated alumina | 400° C. | 56% | 14% | 86 |
| 8 | 86% Titanium dioxide 14% alumina | 300° C. | 5% | 1% | — |
| 9 | 86% Titanium dioxide 14% alumina | 400° C. | 69% | 20% | 80 |
| 10 | 7.7% Cu oxide on activated alumina | 350° C. | 61% | 19% | 91 |
| 11 | 7.7% Cu oxide on activated alumina | 400° C. | 88% | 27% | 82 |
| 12 | 17% Ag on gamma alumina | 300° C. | 7% | 2% | 95 |
| 13 | 17% Ag on gamma alumina | 400° C. | 77% | 24% | 83 |
| 14 | 10% $V_2O_5$ on activated alumina | 300° C. | 23% | 9% | 89 |
| 15 | 10% $V_2O_5$ on activated alumina | 350° C. | 23% | 9% | 91 |
| 16 | 10% $V_2O_5$ on activated alumina | 400° C. | 76% | 23% | 85 |
| 17 | Attapulgus clay | 350° C. | 22% | 8% | 95 |
| 18 | Attapulgus clay | 400° C. | 71% | 22% | 90 |
| 19 | 10% $La_2O_3$ on $Al_2O_3$ | 350° C. | 47% | 13% | 92 |
| 20 | 10% $La_2O_3$ on $Al_2O_3$ | 400° C. | 95% | 20% | 85 |
| 21 | 10% $La_2O_3$ on $Al_2O_3$ | 350° C. | 47% | 19% | 91 |
| 22 | 10% $La_2O_3$ on $Al_2O_3$ | 400° C. | 87% | 23% | 83 |
| 23 | Activated carbon | 350° C. | 20% | 7% | 57 |
| 24 | Activated carbon | 400° C. | 45% | 9% | 80 |
| 25 | 95% Tungsten oxide on activated alumina | 400° C. | 13% | 4% | 75 |
| 26 | Cerium oxide | 400° C. | 19% | 5% | 80 |
| 27 | Bentonite clay | 350° C. | 22% | 7% | 91 |
| 28 | $TiO_2$ | 350° C. | 27% | 11% | 86 |
| 29 | Ti—Zn—Mg oxides | 400° C. | 53% | 6% | 73 |
| 30 | $Cr_2O_3$ | 400° C. | 18% | 4% | 63 |
| Comparative Runs | | | | | |
| C1 | $V_2O_5$ | 400° C. | — | — | — |
| C2 | $PbTiO_3$ | 400° C. | — | — | — |

In the above table, conversion is the amount of liquid feed converted, yield is the yield of difluorotoluene and selectivity is $$\frac{\text{2,3-difluorotoluene}}{\text{2,3-difluorotoluene + 3,4-difluorotoluene}}$$

EXAMPLE 18

The general procedure was followed using 1-(vinyl)-2,2,3,3-tetrafluorocyclobutane as the liquid feed and nitrogen gas as the inert carrier. The reactor was charged with the designated amount of reagent. The results of these experiments are listed in the following table.

TABLE II

| Run | Reagent | Temp. | Conversion | Selectivity |
|---|---|---|---|---|
| 1 | 3 g $Cr_2O_3$ | 400° C. | 10% | 100% |
| 2 | 3 g 19% $Cr_2O_3$ on activated alumina | 400° C. | 62% | 87% |
| 3 | 3 g Attapulgus clay | 400° C. | 85% | 73% |
| 4 | 3 g 20% $Fe_2O_3$ on activated alumina | 300° C. | 4% | 100% |
| 5 | 3 g 10% Cobalt oxide on activated alumina | 300° C. | 3% | 100% |
| 6 | 3 g 19% Manganese oxide on activated alumina | 300° C. | 5% | 100% |
| 7 | 3 g 10% $V_2O_3$ on activated alumina | 400° C. | 67% | 69% |
| 8 | 3 g Rare earth zeolite | 400° C. | 93% | 61% |
| 9 | 3 g 10% $WO_3$ on activated alumina | 400° C. | 47% | 55% |
| 10 | 3 g 98% Zirconium Oxide/2% alumina | 400° C. | 3% | 43% |
| 11 | 5 g 7.7% Cu on activated alumina | 400° C. | 84% | 64% |
| 12 | 5 g 86% $TiO_2$/14% alumina | 400° C. | 94% | 36% |
| 13 | 5 g 17% Ag on gamma alumina | 300° C. | 16% | 38% |
| 14 | 5 g 17% Ag on gamma alumina | 400° C. | 84% | 62% |
| 15 | 5 g 24% Zinc oxide on activated alumina | 400° C. | 68% | 77% |
| 16 | 3.3 g 10% $MoO_3$ on activated alumina | 400° C. | 81% | 53% |
| 17 | 5 g 14% Nickel oxide on activated alumina | 400° C. | 89% | 56% |
| 18 | 5 g $TiO_2$ | 400° C. | 56% | 29% |
| 19 | 5 g $MgO/Al_2O_3$ | 400° C. | 49% | 21% |
| 20 | 5 g 10% ZnO 10% $CrO_2$ on activated alumina | 300° C. | 15% | 47% |
| 21 | 2 g 0.5% $Pd/Al_2O_3$ | 300° C. | 4% | 38% |
| 22 | 2 g 0.5% $Pd/Al_2O_3$ | 350° C. | 20% | 50% |
| 23 | 2 g 0.5% $Pd/Al_2O_3$ | 400° C. | 62% | 61% |
| 24 | 2 g 0.5% $Pd/Al_2O_3$ | 450° C. | 72% | 65% |
| 25 | 2 g 91% $Al_2O_3$ 6% $SiO_2$ | 320° C. | 8% | 59% |
| 26 | 2 g 91% $Al_2O_3$ 6% $SiO_2$ | 340° C. | 10% | 62% |
| 27 | 2 g 91% $Al_2O_3$ 6% $SiO_2$ | 360° C. | 20% | 60% |

TABLE II-continued

| Run | Reagent | Temp. | Conversion | Selectivity |
|---|---|---|---|---|
| 28 | 2 g 91% Al$_2$O$_3$ 6% SiO$_2$ | 380° C. | 33% | 58% |
| 29 | 9 g 99% Al$_2$O$_3$ | 350° C. | 96% | 68% |
| 30 | 8.5 g Cr$_2$O$_3$ | 350° C. | 24% | 57% |
| Comparative Runs | | | | |
| C1 | 7 g SiC | 500° C. | 50% | 40% |
| C2 | 7 g SiC | 550° C. | 93% | 59% |
| C3 | 5 g NaF | 400° C. | 3% | <1% |
| C4 | 5 g NaF | 450° C. | 7% | 19% |
| C5 | 5 g NaF | 500° C. | 41% | 32% |

In the above table
Conversion = (1-(final concentration of starting material/initial concentration of starting material)) × 100
Selectivity = orthodifluorobenzene/(orthodifluorobenzene + others)

EXAMPLE 19

The general procedure was followed using a mixture of 1-(2-chlorovinyl)-2,2,3,3-tetrafluorocyclobutane and 1-chloro-1-vinyl-2,2,3,3,-tetrafluorocyclobutane as the liquid feed and nitrogen gas as the inert carrier. The reactor was charged with 5 g of reagent. The results of these experiments are listed in the following table.

TABLE III

| Run | Reagent | Temp. | Conversion | Product |
|---|---|---|---|---|
| 1 | Al$_2$O$_3$ | 400° C. | 24% | 21% |
| Comparative 1 | SiC | 400° C. | 24% | 0% |
| Comparative 2 | SiC | 450° C. | 61% | <1% |

*Product is a mixture of 1,2-difluoro-3-chloro-benzene and 1,2-difluoro-4-chloro-benzene.

What is claimed:

1. The improvement in the process of preparing substituted fluorobenzenes by pyrolyzing vinylfluorocyclobutanes with two fluorine atoms on the same ring carbon comprising pyrolyzing a vinylfluorocyclobutane of the formula:

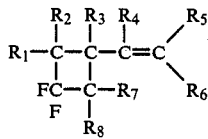

wherein $R_1$ and $R_2$ are independently H, F, CF$_3$, Cl or Br, provided that unless $R_1$ and $R_2$ are both Cl, one of $R_1$ and $R_2$ must be F;

$R_3$ is H, CH$_3$, C$_2$H$_5$ or Cl;

$R_4$ is H, CH$_3$, C$_2$H$_5$ or Cl;

$R_5$ and $R_6$ are independently H, Cl, CH$_3$ and C$_2$H$_5$, provided that one of $R_5$ or $R_6$ must be H, and further provided than when $R_6$ is H, $R_4$ and $R_5$ can be combined to form —CR$_9$=CR$_9$—CR$_9$=CR$_9$— where at least three of the $R_9$ are H and the other $R_9$ can be H, Cl, Br, F or CF$_3$; and $R_7$ and $R_8$ are independently H or CH$_3$, provided that one must be H; at a temperature of 250°–450° C. in the presence of an effective amount of a reagent selected from (i) activated carbon or (ii) a metal oxide selected from the oxides of aluminum, titanium, cerium, or chromium, or mixtures thereof, and further provided if $R_1$, $R_2$ or $R_9$ is CF$_3$, then the reagent must be activated carbon.

2. The process of claim 1 wherein the pyrolyzing is conducted in an inert atmosphere.

3. The process of claim 2 is wherein the inert atmosphere is nitrogen, helium or argon.

4. The process of claim 1 where the metal oxide is in combination with one or more of the oxides of Fe, Co, Ni, Mo, Mn, Zn, Cu, Ag, V, La, W, Zr, Si, Bi, P, or Pb.

5. The process of claim 1 wherein the metal oxide is alumina.

6. The process of claim 1 wherein the temperature is 300° C. to 400° C.

7. The process of claim 1 conducted at a pressure of 0.1 to 10 atmospheres.

8. The process of claim 1 wherein the effective amount is 2 to 10 moles of reagent per mole of starting vinylfluorocyclobutane.

9. The process of claim 1 wherein the substituted fluorobenzene is 1,2-difluorobenzene, the vinylfluorocyclobutane is 1-vinyl-2,2,3,3-tetrafluorocyclobutane and the reagent is Al$_2$O$_3$ or a mixture of Al$_2$O$_3$ and SiO$_2$.

10. The process of claim 1 wherein the reagent is activated carbon and $R_1$, $R_2$ or $R_9$ is CF$_3$.

11. The process of claim 1 wherein $R_3$, $R_4$, $R_5$, $R_6$, $R_7$ and $R_8$ are all H.

12. The process of claim 11 wherein $R_1$ is Br and $R_2$ is F.

13. The process of claim 11 wherein $R_1$ is H and $R_2$ is F.

14. The process of claim 11 where $R_1$ is Cl and $R_2$ is F or Cl.

* * * * *